United States Patent
Lee et al.

(10) Patent No.: US 10,953,063 B2
(45) Date of Patent: Mar. 23, 2021

(54) **METHOD OF TREATING SELECT CANCERS USING TIMED ADMINISTRATION OF PLANT EXTRACT FROM SPECIES *PHYSALIS PUBESCENS* AND *HEDYOTIS DIFFUSA WILLD***

(71) Applicants: Jenny Lee, Sydney (AU); Helen Chui Lan Chai, Sydney (AU)

(72) Inventors: Jenny Lee, Sydney (AU); Helen Chui Lan Chai, Sydney (AU)

(*) Notice: Subject to any disclaimer, the term of this patent is extended or adjusted under 35 U.S.C. 154(b) by 0 days.

(21) Appl. No.: 16/287,005

(22) Filed: Feb. 27, 2019

(65) Prior Publication Data
US 2019/0262413 A1    Aug. 29, 2019

(30) Foreign Application Priority Data
Feb. 27, 2018   (AU) .................. 2018900616

(51) Int. Cl.
| | |
|---|---|
| *A61K 36/748* | (2006.01) |
| *A61K 36/81* | (2006.01) |
| *A61P 35/00* | (2006.01) |
| *A61P 31/18* | (2006.01) |
| *A61P 3/10* | (2006.01) |
| *A61P 35/02* | (2006.01) |
| *A61K 36/75* | (2006.01) |

(52) U.S. Cl.
CPC .............. *A61K 36/81* (2013.01); *A61K 36/75* (2013.01); *A61P 3/10* (2018.01); *A61P 31/18* (2018.01); *A61P 35/00* (2018.01); *A61P 35/02* (2018.01); *A61K 2236/13* (2013.01); *A61K 2236/15* (2013.01); *A61K 2236/17* (2013.01); *A61K 2236/39* (2013.01)

(58) Field of Classification Search
None
See application file for complete search history.

(56) References Cited

U.S. PATENT DOCUMENTS

2019/0336884 A1*  11/2019  Makerri .................. B01D 11/00

FOREIGN PATENT DOCUMENTS

| CN | 105412818 | * | 3/2016 |
| CN | 108543023 | * | 9/2018 |

OTHER PUBLICATIONS

Lin, J. et al. Hedyotis diffusa Willd Extract Suppresses Sonic Hedgehog Signaling . . . In J Oncology 42(2)651-6, Feb. 2013. (Year: 2013).*

* cited by examiner

*Primary Examiner* — Ralph J Gitomer
(74) *Attorney, Agent, or Firm* — Maier & Maier, PLLC

(57) ABSTRACT

A multi time-phase treatment for one of a range of maladies. A dosage form is administered in a first dosage of a therapeutic effective amount of a first plant concentrate or one of its physiological acceptable forms. A dosage form is administered in a second dosage of a therapeutic effective amount of a second plant concentrate or one of its physiological acceptable forms. The first dosage is applied at a first time-phase and the second dosage is applied at a second time-phase spaced from the first time-phase. A combination of the first and second dosage forms administered in at least the first and second time-phases assist in treatment of abnormal cells for treatment for one of the range of maladies.

8 Claims, 1 Drawing Sheet

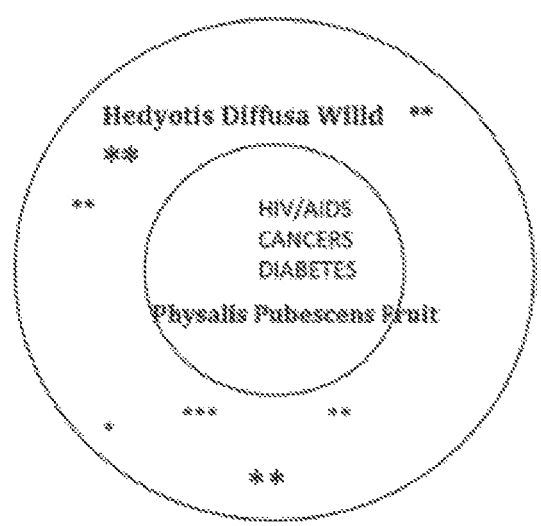

METHOD OF TREATING SELECT CANCERS USING TIMED ADMINISTRATION OF PLANT EXTRACT FROM SPECIES *PHYSALIS PUBESCENS* AND *HEDYOTIS DIFFUSA WILLD*

FIELD

The present invention relates to a treatment regimen using combinations of plant proteins in the treatment of HIV/AIDS infection, cancer, and diabetes.

In particular the present invention relates to methods and compositions for use in treatment of HIV/AIDS, cancer and diabetes. In particular the present invention relates to use of herbal compounds from plant extracts in methods of therapy and the manufacture of medicaments as well as compositions containing these compounds.

The invention has been developed primarily in the use of plant extracts and herbal compounds for treating HIV/AIDS, cancer, and diabetes, and will be described hereinafter with reference to this application. However, it will be appreciated that the invention is not limited to this particular field of use.

BACKGROUND

Human Immunodeficiency Virus (HIV), the etiological agent for AIDS (Acquired Immune Deficiency Syndrome) is a virus infection caused by weakened immune system. Most importantly, HIV infects and destroys CD4+ cells which are critical to the immune system and hence renders the patient susceptible to opportunistic infections resulting in progressive, irreversible neoplasm. HIV is neurotropic, capable of infecting monocytes and macrophages in the central nervous system causing severe neurologic damage. Most anti-HIV drugs aim at inhibiting the viral enzymes, reverse transcriptase, thereby inhibiting de novo infection of cells.

Chemotherapies and radiation therapy are recognized as the mainstream approaches to the treatment for HIV/AIDS infection and cancer. Such conventional treatments however suffer a number of drawbacks including: (i) severe side effects—for example, drugs used in chemotherapies characteristically damage and/or destroy cells that grow rapidly, such as cancer cells, also affect rapidly growing normal cells such as blood cells in the bone marrow, cells in the hair follicles, and the cells that generate sperm in the testes; and (ii) drug resistance—cancer cells have the ability to develop drug resistance to chemotherapeutic agents over time, for example the development of cisplatin resistance is a major source of treatment failure over time in non-small cell lung cancer.

Drug resistance and cytotoxicity against non-tumor associated cells limits the extended usage and the therapeutic effectiveness of angiogenesis inhibitors. Continual global research for more effective multi-target constituents that promotes cancer cell apoptosis in genetic pathway with no side-effect stands as an ultimate goal for this tumoricidal activity.

The search for more effective therapies to treat HIV/AIDS and cancer is still to date of paramount importance. However, with the rapid social progress and the ever changing lifestyle, more and more people are opting for natural, healthier alternative approach to their medical issues. Most prescription medication, over-the-counter medicine, and vitamin supplements contains fillers and chemicals that triggers many side effects and are extremely hazardous to the human body.

One object of the invention is to provide alternative medicines for treatment of AIDS, cancer and diabetes that do not have the above drawbacks.

The present invention seeks to provide an improved treatment for HIV/AIDS and cancers, which will overcome or substantially ameliorate at least one or more of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY

In a first aspect of the invention there is provided a multi time-phase treatment for one of a range of maladies comprising: administering a dosage form in a first dosage of a therapeutic effective amount of a first plant concentrate or one of its physiological acceptable forms; and administering a dosage form in a second dosage of a therapeutic effective amount of a second plant concentrate or one of its physiological acceptable forms; wherein the first dosage is applied at a first time-phase and the second dosage is applied at a second time-phase spaced from the first time-phase; and wherein combination of the first and second dosage forms administered in at least the first and second time-phases assist in treatment of abnormal cells for treatment for one of the range of maladies.

The multi time-phase treatment regimen shows a surprising effect in combination when dosage forms are administered spaced apart.

Preferably the second time phase is spaced from the first time-phase to allow for sufficient time for ingestion and transfer to the treating location.

Preferably the first dosage of the therapeutic effective amount of the first plant concentrate is ingested at a first time-phase early in the day and provides an aggressive disruptive effect to abnormal cells and the second dosage of the therapeutic effective amount of the second plant concentrate is ingested at a second time-phase at least two hours later and provides a following destructive effect to the disrupted abnormal cells.

Preferably the dosage forms of the first and second plant concentrates or one of its physiologically acceptable forms are administered at first and second time-phases between three to six hours apart.

Preferably the multi time-phase treatment of administering a dosage form in a first dosage of a therapeutic effective amount of a first plant concentrate or one of its physiological acceptable forms at a first time-phase in a day and administering a dosage form in a second dosage of a therapeutic effective amount of a second plant concentrate or one of its physiological acceptable forms at a second time-phase later in the day is repeated daily for weeks to months or until the malady is tested to have been reduced, removed or stabilised.

Preferably the first plant concentrate or one of its physiologically acceptable salts is obtained from *Physalis Pubescens* fruit (PPF).

Preferably *Physalis pubescens* fruit of the first dosage is provided in a dosage of between about 15 to 25 grams.

Preferably the second plant concentrate or one of its physiologically acceptable salts is obtained from *Hedyotis Diffusa* Willd (HDW).

Preferably *Hedyotis Diffusa* Willd of the second dosage is provided in a dosage of between about 15 to 25 grams.

Preferably in the combined treatment, *Physalis pubescens* fruit and *Hedyotis Diffusa* Willd can be provided in a dosage form in a ratio of between about 1:1 to 1:5.

Preferably the first plant concentrate or one of its physiologically acceptable salts is administered before administration of the second plant concentrate or one of its physiologically acceptable salts.

Preferably the *Physalis pubescens* fruit and *Hedyotis Diffusa* Willd are provided in a treatment regimen whereby dosages are administered in a predetermined spaced apart timing and amount, wherein *Physalis pubescens* fruit is administered initially followed by *Hedyotis Diffusa* Willd in a ratio of between about 1:1 to 1:5.

Preferably the at least first and second natural plant extracts are combined for treatment of HIV/AIDS infection, various cancers and diabetes.

In a preferred embodiment both plant concentrates are prescribed at 15 ml orally, per treatment session for its pharmaceutically effectiveness, this could include a morning dose of 15 ml PPF, then 15 ml HDW at noon followed by 15 ml HDW, night. The ratio is work on 1:1 for PPF concentrate and HDW concentrate, and treatment dosage are given accordingly to stages and severity of illness. Where severity of disease is high, dosage of 20 ml to apply over the course of treatment. Therefore the range is 15 ml to 20 ml. The dosage regimen is continued on a repeat bases at a controlled/adjusted amount after recovery as supplement for health and vitality.

Preferably the at least first and second forms plant concentrates are for treatment of one of: a. HIV/AIDS, b. various cancers and c. diabetes.

In a related aspect of the invention there is disclosed a combined treatment regimen for HIV/AIDS infection, various cancers and diabetes comprising: administering a dosage form of a plant protein extract or one of its physiologically acceptable salts obtained from enzymes of *Physalis pubescens* fruit, in a therapeutically effective amount at a predetermined period; administering a dosage form of a plant protein extract or one of its physiologically acceptable salts obtained from *Hedyotis Diffusa* Willd, in a therapeutically effective amount at a predetermined period; and wherein the dosage forms in combination induce apoptosis in affected cells.

By combining two plant protein extracts in a prescribed dosage regimen by a multi-phase administration, the applicant has found that the treatment is able to improve targeting of tumorcidalactivity in HIV/AIDS infection, various cancer and diabetes.

In one embodiment the dosage forms are compounded into a topical cream, wherein the cream is applied to a surface of a body one at a time at predetermined spaced intervals so that effective penetration of a first of the dosage form occurs across the dermis and cell membrane in advance of the second, and wherein amounts of the dosage forms are effective for initiating and propagating apoptosis of affected cells.

In an alternate embodiment, the dosage forms can be provided in a powdered form or tablet or capsule form for oral administration. A further alternative can include liquid form in aqueous or non-aqueous injectable media.

Without being bound by theory, the applicant believes the action of the combined treatment regimen disposes an effected cell to disruption followed by destruction. The treatment regimen allows higher rate of apoptosis by first diminishing affected cells capability of accelerated division. Hence there appears to be a synergy between the active ingredients in treatment of affected cells.

A further benefit of the present treatment is that the combination of natural plant proteins substantially reduces the prospect of resistance, and there is less likelihood of acute side effects observed in conventional treatment therapies.

In one embodiment, the combined treatment can further include administering a supplementary therapeutic effective amount of a dosage form from the second natural plant protein extract or one of its physiological acceptable salts, wherein the supplementary dosage of the second extract or one of its physiologically acceptable salts is administered in a predetermined phased cycle after administration of the second natural plant protein extract or one of its physiologically acceptable salts.

The administration of a supplementary dosage of *Hedyotis Diffusa* Willd appears to have a potent effect on residual disease cells. The combined treatment can be a multi timephase dosage of a morning dosage of *Physalis pubescens* fruit; a second time phase dosage of *Hedyotis Diffusa* Willd later in the day; and a third time phase evening dosage of *Hedyotis Diffusa* Willd, wherein the three time phased dosage administration is repeated for an effective treatment period. Preferably this is repeated daily for weeks to months or until the malady is tested to have been reduced, removed or stabilised.

In a related aspect of the present novel invention, there is disclosed a pharmaceutical composition for the treatment of HIV/AIDS infection, various cancers and diabetes comprising: an effective amount of a plant concentrate or one of its physiologically acceptable salts obtained from *Physalis pubescens* fruit; and an effective amount of a plant concentrate or one of its physiologically acceptable salts obtained from *Hedyotis Diffusa* Willd.

Preferably *Physalis pubescens* fruit and *Hedyotis Diffusa* Willd are administered in an oral dosage form spaced apart in a multi time-phase predetermined timing wherein apoptosis is induced in affected cells.

The treatment period is continued until all carcinogenic cells are cleared/"eaten". During this process, PPF will provide nourishment adding its spectrum of pharmacological & tonic effects. HDW further completes the treatment process.

Preferably in use, an effective amount of the plant concentrate or one of its physiologically acceptable salts obtained from *Physalis pubescens* fruit is administered at a first predetermined period, this being repeated cyclically to maintain an effective amount or concentration systemically.

Preferably in use, an effective amount of the plant concentrate or one of its physiologically acceptable salts obtained from *Hedyotis Diffusa* Willd is administered at a second predetermined period, this being repeated cyclically to maintain an effective amount or concentration systemically.

Preferably in use, an effective amount of the plant concentrate or one of its physiologically acceptable salts obtained from *Hedyotis Diffusa* Willd is administered at a third predetermined period, this being repeated cyclically to maintain an effective amount or concentration systemically.

Preferably in one embodiment the ratio of *Physalis pubescens* fruit:*Hedyotis Diffusa* Willd is 1:1.

The pharmaceutical composition can contain regular excipients that are acceptable in the process of drug manufacturing, such as binders, fillers, preservatives, flow control agents, softeners, wetting agents, dispersing agents, emulsifiers, solvent, antioxidants and/or propellants, drug carriers.

The pharmaceutical compositions can contain one or more of the following substances as fillers: sugars and their derivatives (lactose, modified lactose, sucrose, glucose, mannitol, modified mannitol, fructose), polysaccharides (cellulose and its derivatives, starch, modified starch), dextrin, dextrose, dextrate, maltodextrin, calcium and its salts, (phosphates, carbonates, chlorides), magnesium and its derivatives (oxide, carbonate, stearate), crospovidone, copovidone, cyclodextrines, alginic acid and its salts, saccharine and its salts, sodium and its salts (chloride, citrate, fumarate, carbonate), aspartame, lactic acid and its salts, succinic acid, ascorbic acid, tartaric acid, colloidal silicon dioxide, cyclamate, benzoic acid and its salts, parabens and their salts.

In a further related aspect there is disclosed a method of treatment of HIV-infection, cancer, and diabetes comprising administering a therapeutically effective amount of a pharmaceutical composition having: an effective amount of a plant concentrate or one of its physiologically acceptable salts obtained from *Physalis pubescens* fruit; and an effective amount of a plant concentrate or one of its physiologically acceptable salts obtained from *Hedyotis Diffusa* Willd.

In a further related aspect the present invention also relates to the use of: an effective amount of a plant concentrate or one of its physiologically acceptable salts obtained from *Physalis pubescens* fruit in a pharmaceutically acceptable carrier; and an effective amount of a plant concentrate or one of its physiologically acceptable salts obtained from *Hedyotis Diffusa* Willd in a pharmaceutically acceptable carrier; in the manufacture of a medicament for administration to a patient in the therapeutic treatment of HIV/AIDS, cancer, or diabetes.

In yet a further related aspect the present invention also relates to the use of: an effective amount of a plant concentrate or one of its physiologically acceptable salts obtained from *Physalis pubescens* fruit in a pharmaceutically acceptable carrier; and an effective amount of a plant concentrate or one of its physiologically acceptable salts obtained from *Hedyotis Diffusa* Willd in a pharmaceutically acceptable carrier; wherein predetermined dosages of the respective plant concentrate is administered in a dosage form for the manufacture of a pharmaceutical composition for the therapeutic treatment of HIV/AIDS, cancer, or diabetes.

In yet a further related aspect, there is provided a pharmaceutical composition when used in the treatment of HIV/AIDS, cancer, or diabetes, wherein the composition comprises pharmaceutically acceptable plant concentrate of *Physalis pubescens* fruit and *Hedyotis Diffusa* Willd dosed apart in a ratio of about 1:1 to 1:5.

In a further related aspect of the present invention there is described a pharmaceutical composition for use in a method for prevention or treatment of cancers including liver, ovarian, kidney, stomach, prostate, breast, skin, throat, colon, lymph, cervical, nasal cavity, said composition comprising as an active ingredient a therapeutically effective amount of:
I. a plant concentrate or one of its physiologically acceptable salts obtained from *Physalis pubescens* fruit in a pharmaceutically acceptable carrier; and II. a plant concentrate or one of its physiologically acceptable salts obtained from *Hedyotis Diffusa* Willd in a pharmaceutically acceptable carrier; and wherein the first and second compositions are administered spaced apart on a daily basis so as to substantially improve absorption of a first of said concentrates before administering the second.

In another aspect, the invention provides a kit comprising: (a) at least one plant concentrate or one of its physiologically acceptable salts obtained from *Physalis pubescens* fruit; and (b) at least one of a plant concentrate or one of its physiologically acceptable salts obtained from *Hedyotis Diffusa* Willd in a pharmaceutically acceptable carrier. Optionally, each of the combined plant concentrate is provided in a separate dosage form. The kit of the invention may facilitate combined treatment using different modes of administration for each compound as well as different duration of treatment.

In a further related aspect the present invention relates to the synthesis of plant extract, *Physalis pubescens* fruit and *Hedyotis Diffusa* Willd. Through advanced reflux extraction technology, the fresh extract contains the concentrates, which in combination have a significant improved anti-tumor and anti-HIV properties, and to uses therefore to enhance cell resistance, inhibit growth of malignant cells and ultimately for curing of HIV/AIDS, cancer and diabetes.

The reflux extraction process involves applying distilled water for cleaning of PPF and HDW, pressing and moved by a screw conveyor to resolution and resolve, grinding, extraction and ultra-filtrating of concentrate.

It can be seen that the invention of provides the benefit of less severe side effects associated with conventional therapy, and decrease in development of infection resistance due to the combined treatment and composition.

In one form the invention provides a medicinal herb substance formulation. A plant based formulation composing in particular MAP30, an anti-HIV protein. This protein organic matter obtainable from the fruit enzymes of PPF contains also an obvious anti-cancer physiological protein and Polypeptide-P (plant insulin), and when coordinated with HDW, produced a double-action effectiveness for treating various cancer, HIV/AIDS infection and diabetes. Polypeptide-P is a safe natural source containing significantly high levels of blood sugar lowering compound useful for diabetes sufferers as noted in medical studies. Research findings disclosed the natural bio chemical 2-Hydroxy-3-Methylanthraguinone, as contained in HDW can promote immune response and significantly ceased carcinogenesis activity, for instance, it induces apoptosis in human leukemia cells.

In a further related aspect of the invention there is disclosed a method for prevention or treatment of cancers including liver, ovarian, kidney, stomach, prostate, breast, skin, throat, colon, lymph, cervical, nasal cavity, the method comprising administration at differential times comprising at least two phases, a first therapeutically effective amount of a plant concentrate or one of its physiologically acceptable salts obtained from *Physalis pubescens* fruit in a pharmaceutically acceptable carrier during the morning phase; a second therapeutically effective amount of a plant concentrate or one of its physiologically acceptable salts obtained from *Hedyotis Diffusa* Willd in a pharmaceutically acceptable carrier during in the second afternoon phase; and optionally a third therapeutically effective amount of a plant concentrate or one of its physiologically acceptable salts obtained from *Hedyotis Diffusa* Willd in a pharmaceutically acceptable carrier during in the third evening phase.

The invention further relates to a method of treatment of HIV-infection, cancer, and diabetes comprising administering a therapeutically effective amount of a pharmaceutical composition having: an effective amount of a plant concentrate or one of its physiologically acceptable forms obtained from *Physalis pubescens* fruit; and an effective amount of a plant concentrate or one of its physiologically acceptable forms obtained from *Hedyotis Diffusa* Willd; Use of: an effective amount of a plant concentrate or one of its physiologically acceptable forms obtained from *Physalis pubescens* fruit in a pharmaceutically acceptable carrier; and an effective amount of a plant concentrate or one of its physiologically acceptable forms obtained from *Hedyotis Diffusa* Willd in a pharmaceutically acceptable carrier, in the manufacture of a medicament for administration to a patient in the therapeutic treatment of HIV/AIDS, cancer, or diabetes; Use of: an effective amount of a plant concentrate or one of its physiologically acceptable forms obtained from *Physalis pubescens* fruit in a pharmaceutically acceptable carrier; and an effective amount of a plant concentrate or one of its physiologically acceptable forms obtained from *Hedyotis Diffusa* Willd in a pharmaceutically acceptable carrier; for the manufacture of a pharmaceutical composition for the therapeutic treatment of HIV/AIDS, cancer, or diabetes.

The invention further relates to a method for prevention or treatment of cancers including liver, ovarian, kidney, stomach, prostate, breast, skin, throat, colon, lymph, cervical, nasal cavity, the method comprising administration at differential times comprising at least two time-phases, a first therapeutically effective amount of a plant concentrate or one of its physiologically acceptable forms obtained from *Physalis pubescens* fruit in a pharmaceutically acceptable carrier during the morning phase; a second therapeutically effective amount of a plant concentrate or one of its physiologically acceptable forms obtained from *Hedyotis Diffusa* Willd in a pharmaceutically acceptable carrier during in the second afternoon time-phase; and optionally a third therapeutically effective amount of a plant concentrate or one of its physiologically acceptable forms obtained from *Hedyotis Diffusa* Willd in a pharmaceutically acceptable carrier in a third evening time-phase.

Without being bound by theory, applicants have found that spaced apart administration of therapeutically effective dosages of *Physalis pubescens* fruit and *Hedyotis Diffusa* Willd according to the invention initially disrupts affected cells and exposes disrupted cells to destruction by presenting effective dosage(s) of *Hedyotis Diffusa* Willd.

Other aspects of the invention are also disclosed.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which:

FIG. 1 is A coordinated botanical medicament in accordance with a preferred embodiment of the present invention; and

DETAILED DESCRIPTION

It should be appreciated that while these techniques are exemplary of preferred embodiments for the practice of the invention, those of skill in the art, in light of the present disclosure, will recognize that numerous modifications can be made without departing from the spirit and intended scope of the invention.

By way of example, the formulations and treatments which follow are not intended to be limiting, and are provided for illustrating the efficacy of the inventive concept on improving apoptosis of infected cells and decreasing virus resistance and diminishing side effects in vitro and in-vivo.

Treatments

The terms "treating" and "treatment" as used herein refer to reduction in severity and/or frequency of symptoms, elimination of symptoms and/or underlying cause, prevention of the occurrence of symptoms (prophylaxis) and/or their underlying cause, and improvement or remediation of damage.

Thus, for example, the present method of "treating" a condition encompasses both prevention of the condition in a predisposed individual, treatment of the condition in a clinically symptomatic individual and treatment of a healthy individual for beneficial effect.

"Treating" as used herein covers any treatment of, repair or prevention of a condition in a mammal, particularly a human, and includes inhibiting the condition, i.e., arresting its development; or relieving or ameliorating the effects of the condition, i.e., cause regression of the effects of the condition and producing a beneficial effect.

"Prophylaxis" or "prophylactic" or "preventative" therapy as used herein includes preventing the condition from occurring or ameliorating the subsequent progression of the condition in a subject that may be predisposed to the condition, but has not yet been diagnosed as having it.

As used herein, "condition" refers to any deviation from normal health and includes a disease, disorder, defect or injury, such as injury caused by trauma, and deterioration due to inflammatory response. Conditions in which the oral composition administration is beneficial generally fall into the categories of those in which involve treatment of HIV/AIDS, cancer and diabetes.

Detailed discussion on clinical conditions which can be treated or prevented by pharmaceutical compositions of the present invention is presented further below. At this point, it should be understood that, in general, for the purpose of therapeutic applications pharmaceutical compositions are administered in an amount sufficient to cure or at least partially arrest, ameliorate, reduce or delay the onset of symptoms of a clinical condition and its complications, referred to herein as a therapeutically effective amount or dose. Amounts effective for this use will depend upon severity of the condition and the general state of a patient. Single or multiple administrations on a daily, weekly or monthly schedule can be carried out with predetermined dose levels and pattern.

In other specific embodiments, methods and compositions of the invention are intended for the treatment of a malignancy. In cancerous situations, modulation of the T cell balance may be in the direction of inducing a pro-inflammatory response or in augmenting the anti-tumor associated antigens immunity. As used herein to describe the present invention, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the compositions of the present invention may be used in the treatment of non-solid and solid tumors.

By "patient" it is meant any mammal who may be affected by the above-mentioned conditions, and to whom the treatment and diagnosis methods herein described is desired, including human, bovine, equine, canine, murine and feline subjects. Preferably, the patient is a human. Administering of the composition according to the method of the invention to the patient includes both self-administration and administration to the patient by another person.

Administration

The dosage forms are administered in a substantially pure form or together with a pharmaceutically acceptable carrier for oral administration.

The composition can be administered by any suitable route, and the person skilled in the art will readily be able to determine the most suitable route and dose for the condition to be treated and the subject. The composition can be administered orally, in dosage unit formulations containing conventional non-toxic pharmaceutically acceptable carriers, adjuvants, and vehicles.

A typical daily dosage might range from about 15 ml to up to 30 ml or more in a oral dosage form. The usefulness of an oral formulation requires that the active agent or combinations thereof according to the invention are bio-available. Bioavailability of orally administered drugs can be affected by a number of factors, such as drug absorption throughout the gastrointestinal tract, stability of the drug in the gastrointestinal tract, and the first pass effect. Pharmaceutical compositions suitable for oral administration are typically solid dosage forms (e.g., tablets) or liquid preparations (e.g., solutions, suspensions, or elixirs).

Liquid dosage forms also allow subjects to easily take the required dose of active ingredient. Liquid preparations can be prepared as a drink, or to be administered, for example, by a naso gastric tube (NG tube). Liquid oral pharmaceutical compositions generally require a suitable solvent or carrier system in which to dissolve or disperse the active agent, thus enabling the composition to be administered to a subject. A suitable solvent system is compatible with the active agent and non-toxic to the subject. Typically, liquid oral formulations use a water-based solvent.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention will now be described by way of reference only to the following non-limiting examples.

Example 1: Determine the Effect of Treatment Regimen Using a Composition and Method of Treatment on Infected Cell Activity Methods and Treatment Human subjects were requested to consume an oral composition according to first composition (refer above). Blood sampling was taken and completed immediately before oral administration and at three hours after ingestion of the measured volume.

Plasma was isolated from collected blood samples, and concentration measured. Dosing continued until protease, which are vital catalytic mechanism, resumed normal functioning. Most stages of cells proliferation results from swelling of protease secretion, causing disorientation in the physiological role of hormones, antibodies or other enzymes.

Treatment

This example examines if expression of protein levels are decreased by a composition according to the invention in the presence of inflammatory stimuli. As in example 2 (above), affected cells were exposed to a dosage form of a plant concentrate or one of its physiologically acceptable salts obtained from *Physalis pubescens* fruit, in a therapeutically effective amount at a predetermined period 1 to 3 hours and then activated with a dosage form of a plant concentrate or one of its physiologically acceptable salts obtained from *Hedyotis Diffusa* Willd, in a therapeutically effective amount at a predetermined period for 3 hours.

This fresh concentrated composition and digestibility value directly translate and visibly rouse up internal body immune system to defence efficiency, strengthen cell immunity. to combat cancer ability and additionally, the use of native plant extract shows 80% more potency in absorption, works stronger and better assimilation rate than would tablet or capsule.

Because cited, comprising mixture therein disclosed that synthesis of these extract holds a wide volatile effectiveness to health hazards and improve handling properties. Fruity, yet citrusy in taste when semi-ripe, PPF contains pectates, physanol and its bio-vitality properties can accelerates overall body metabolism.

Both native plant extract are prescribed at 15 ml orally, per treatment session for its pharmaceutically effectiveness, i.e a morning dose of 15 ml PPF, then 15 ml HDW at noon followed by 15 ml HDW, night. The ratio is work on 1:1 for PPF extract and HDW extracts, and treatment dosage are given accordingly to stages and severity of illness. Where severity exceeds, dosage of 20 ml to apply over the course of treatment. Therefore the range is 15 ml-20 ml The mode of action follows that administering the native extract of PPF immune cells against proliferations, topological inactivation of viral DNA with its "eat" carcinogenic actions. The applied dose of HDW further cleanses entire body systems, scans and induces apoptosis of the killer cells. The time-dose intervals mediate the extract potency assimilation period in the body, thus enhances the double herb interface efficacy and thereby encoding the effectiveness.

Fragrance, taste and color of organic matter remain unchanged through the process of scientific preparation, to retain its original pure effectiveness and nourishment without any side effect. These herb has refreshing, cooling properties and is suitable for all patients' diagnosis. The cancer cell are characterized by uncontrolled proliferation and therefore exhibiting the proliferation of tumor cells as swelling of protease secretion is one of the key approaches for the development of anti-cancer drug. Cancer poised a serious global health problem. No cure has yet been documented other than a relieving therapy.

The advantages of the invention include:

The treatment regimen of the invention has relatively no side effects and can be used as an alternative remedy for various symptoms of diseases.

The invention will improve nation economy, social development, contribute new research achievement, up-hold general well-being of society and also significance recognition.

Enhance energy, Increase mental alertness and less fatigue.

Improved breathing (reduce breath shortness) for heart condition sufferers

Preparation/Extraction Methods.

The preparation of the specific steps PPF and HDW native extract of the present invention are as follows:

Step 1

Fresh *Physalis Pubescens* Fruit (PPF) is cleaned with distilled water; using rotary cool evaporator for drying until all water has utterly evaporated. Pressing a perforated tube is used in the press straining process resolving the pericarp, pectates, mucilage and seeds from the fruit. Following step then involves crushing the seeds, grinding and macerating of the pericarp to blend with filtrate. Natural preservative is added to extend shelf-life of the native extract.

Step 2

Fresh *Heydotis Diffusa* Willd (HDW) is cleaned with distilled water. Using rotary cool evaporator drying until all water has utterly evaporated. Grinding and using reflux extraction method, repeating three times and ultra-filtration on final concentration to reserve a pure filtrate. Natural preservative is added to extend shelf-life of the native extract.

Liquid Extract—Response Relationship

Once PPF extract enters the body, the physiological protein readily assimilates and utilizes its carcinogen "eat" capability to act on the described case. Subsequently, coordinating with the anti-cancer component in HDW extract to fortify treatment and thereby, significantly provoke the killing off several cancer cell lines, including leukemia, breast, stomach, enteritis, oesophagus, uterus, lung, liver, lymph, prostate and pancreatic cancer lines.

In the manner of treatment for HIV/AIDS infection and of diabetes, a daily double dosage (morning and night) of PPF extract followed by a standard midday dose of HDW extract will quantifies the cell exposure. Contrary to cancer treatment, a single daily dosage of PPF extract coordinated with double dosage (noon & night) of HDW extract to induce cell cycle arrest and apoptosis. The dose-time frequency is linear dependent on illness severity. In general, supplementing daily intake with PPF alone can encode its botanical efficacy and increases resistance in overall health.

This treatment of double herbs' compound also contains Polypeptide-P (plant insulin), suitable for diabetes sufferer to balance blood sugar level.

Referring to FIG. 1, oral administration of PPF to target the various illnesses of HIV/AIDS, Cancers and or diabetes as Illustrated in inner circle 1.

Coordination of HDW coats the outer layer clearing missed targets of these killer cells, as described with symbols***, while additionally add nourishment to body with its biochemical properties.

Case Studies and Examples

Case 1—Cervical Cancer

In a first example, a 27-year old woman (the patient) was diagnosed with stage two cervical cancer. The patient was administered with a morning (first) time-phase dosage of 10 ml liquid concentrate of *P. Pubescens* Fruit. The first time-phase was followed by administration of a second time-phase liquid dose of 12 ml of a concentrate derived from *H. Diffusa* Willd at or close to midday. The patient was subsequently administered with a further third night time-phase liquid dosage of 12 ml of *H. Diffusa* Willd.

All of the first, second and third time-phase dosages were administered one hour before meal time consecutively. The three time-phase treatment regimen was repeated over a three-month period and it was observed over this period that not only did the patient feel more energetic over the three month treatment period, but imaging reported disappearance of cervical cancerous cells. This observation therefore suggests there are cytotoxicity activities and synergistic effects between the two specific native extracts administered in a two or three phase treatment regimen.

Case 2—Breast Cancer

In this case, a 45-year old woman (the patient) presented with advanced triple negative Stage three breast cancer. The patient was previously advised that the primary treatment program for the diagnosed condition was a course of chemotherapy.

Being aware of various unpleasant side-effects of chemotherapy sessions, the patient acceded to a treatment in accordance with the present invention. The patient was administered with a first time-phase morning dose comprising 15 ml of concentrate *P. Pubescens* Fruit concentrate followed with 15 ml of *H. Diffusa* Willd concentrate at the second midday time-phase, and a third evening time-phase dosage of 15 ml repeat dose of *H. Diffusa* Willd concentrate. In this case, the patient was administered a stronger first phase dosage due to the diagnosed disease severity.

All dosages in each dosage phase were administered one hour before taking food. Regular interval imaging documented rejuvenation of healthy cells at the metastatic site. This finding suggests there is strong potential significance in this concentrates for breast cancer treatment. The patient was later found to be in remission and cancer free.

Case 3—Prostate Cancer

A man (the patient) aged in his 30's was diagnosed with prostate cancer. The patient was experiencing unexplained symptoms including weight lost, frequent or sudden need to urinate. The patient was referred to the applicant for treatment by the present inventive method. The patient was treated with a morning phase dose of 12 ml of native *P. Pubescens* Fruit extract, a second phase midday dose of 14 ml of *H. Diffusa* Willd and a third phase evening dosage of 14 ml *H. Diffusa* Willd. All dosages were administered orally one hour before meals.

It was observed four weeks into treatment that the patient's urination symptoms had been relieved, i.e., less frequent, and a feeling of significant improvement in overall health. Repeated imaging of the patient during treatment showed gradual reduction of tumorous cells. Applicant believes this observation indicates the extract, under the applied regimen have produced a surprising synergistic effects.

Case 4—Acute Myeloid Leuka Mia (AML)

A 21-year old boy (the patient) was diagnosed with acute myeloid leukaemia (AML). The patient presented showing signs of constant tiredness, weight loss, lack of energy, loss of appetite, emotionally depressed and constant headaches. Clinical evaluation had the patient preparing for chemotherapy treatment. In this case, the patient decided to undergo applicant's treatment regimen.

The patient was administered a first morning phase dosage of 14 ml of *P. Pubescens* Fruit concentrate, followed by a second midday phase of 16 ml *H. Diffusa* Willd concentrate followed by a third evening phase dosage of 18 ml *H. Diffusa* Willd concentrate. All dosages were administered one hour prior to meals. The treatment continued for a continual period of four months.

Hospital scans taken during the treatment period showed significant improvement in the patient's condition. The patient in this case continued treatment according to the phase 1 to 3 dosage regimen for a further two months and subsequently original symptoms were substantially eliminated.

Case 5—HIV/AIDS

A man (the patient) aged 24 presented with diarrhea. The patient worked at a busy recreational club and had developed diarrhea within several months of presenting to his general practitioner (GP). The patient's GP diagnosed the patient had inflammation in the colon and prescribed a course of oral antibiotics. However, the underlying cause of the patient's symptoms was not identified.

Over a period of time the patient progressively lost weight, had a fever, and general fatigue persisted. The oral antibiotic treatment was therefore not effective and symptoms continue.

Several available drugs were prescribed by the GP and none showed effectiveness in relieving symptoms of the patient. Intensive clinical examinations of the patient were performed and revealed several immunologic abnormalities. In particular, the patient was found to have a decreased number of CD4, i.e., 198 (the normal count being 500-1500), therefore a positive indication for AIDS infection.

The patient elected to take a course of treatment according to the applicant's invention by administering on a daily routine before meals a first morning time-phase dosage of 20 ml of *P. Pubescens* Fruit concentrate, a second time-phase midday dosage of 18 mls of *H. Diffusa* Willd concentrate, and a third evening time-phase dosage of 20 mls *H. Diffusa* Willd concentrate.

Observations showed that the patient started feeling mentally refreshed and able to sustain days at work. Clinical scans observed the gradual reduction of the viral load with CD4 counts regaining stability, Patient dosing continued for six months wherein a comprehensive imaging detected no signs or recurrence of the viral activities. No side effects were observed. This indicates there is a positive synergistic potential of this extract regimen for HIV/AIDS, Case 6—Skin & Stomach Cancer A woman (the patient) in her 50's was diagnosed with both skin and stomach cancers during a routine visit to a GP. A second opinion was sought for a small albeit suspicious looking sun spot appearing to be metastatic melanoma. The patient was diagnosed with enlarged lymph nodes filled with proliferating cancer cells. Then with additional symptoms of abdominal discomfort, loss of appetite, which there was concern she may have a peptic ulcer. The patient had an upper endoscopy which showed a large ulcerated tumor in the body of the stomach.

The first decision regarding management is whether to resect it immediately or to administer preoperative chemotherapy or radiation therapy. Either curative treatment was uncertain of the tumor recurrence given the side effects that follows with conventional therapy. The patient decided to trial the applicant's-treatment regimen in accordance with the present invention. The patient was administered a daily repeated regimen of a first morning time-phase dosage of 18 mls of *P. Pubscens* Fruit concentrate; a second midday phase dosage of 15 mls of *H. Diffusa* Willd concentrate; and a third phase dosage of 20 mls of *H. Diffusa* Willd concentrate. All dosages were administered one hour prior to meals.

The patient adhered to the treatment regimen and signs of promising effects at three months were detected. The patient subsequently is in remission and substantially free of disease today without drawbacks. Applicant believes this shows there is strong efficacy and effectiveness of the treatment regimen through the combined phased administration of effective therapeutic amounts of *P. Pubscens* Fruit concentrate and *H. Diffusa* Willd concentrate.

Case 7—Lymph Cancer

In this case a 60-year old man (the patient) presented to medical practitioner with complaints of lack of stamina, unable to sit over long period and evolving increasing pain leading to sleepless nights. The patient worked as an electrical engineer over 35 years. Medical diagnosis referred the patient from primary care to back pain therapy due to history of disc herniation.

Further medical screening and testings of the patient determined the patient was suffering from lymphoma with metastasis to lumbar spine area.

The patient was administered a first time-phase morning dosage of 18 mls of *P. Pubscens* Fruit concentrate. This was followed by second time phase midday dosage of 16 mls of *H. Diffusa* Willd concentrate and a third time-phase evening dosage of 20 mls of *H. Diffusa* Willd concentrate. All dosages were administered in an oral form about one hour before meals. Approximately two and a half months later, the patient discovered increased stamina and improved quality of sleep. Applicant believes further screening supports this multi-phased treatment approach using a synergistic timed combination of *P. Pubscens* Fruit concentrate and *H. Diffusa* Willd concentrate.

Case 8—Nasal Cavity & Throat Cancer

A 43-year old singer/actor (the patient) presented with a case of nasal cavity and throat cancers. The patient complained of hoarseness of voice for at least four months. The pathologic diagnosis was squamous cell carcinoma in situ, based on examination of a biopsy specimen obtained by resection of the lesion.

The nasal cavity cancer caused eye watering, rhinorrhoea, nasal obstruction, visual changes, facial pain and headaches. The patient had no significant medical family history or taking any medication.

Typical treatment of the patient's described situation requires aggressive surgery, and combined chemotherapy and radiotherapy. Prognosis in this case was poor.

The patient elected to try the applicant's combined multi-phased treatment instead of conventional treatment fearing the outcomes would compromise vocal career. The patient was administered first time-phase dosage of 18 mls of *P. Pubscens* Fruit concentrate in the mornings, followed by a second time-phase midday dosage of 16 mls of native *H. Diffusa* Willd concentrate and a third evening time-phase dosage of 20 mls of *H. Diffusa* Willd concentrate.

Routine clinical imaging was performed over a sustained period of daily multi-phase treatment and observation made that the cytotoxic effects on both types of cancer cells and signs of apoptosis process.

Case 9—Kidney Cancer

A 71-year old person (the patient) presented with a recently twisted back from golfing and sought regular chiropractic relief/care since the patient has a medical history of back pain. After a number of visits and chiropractic treatments, pain persisted and pain worsened to a point of being excruciating and constant.

The patient's clinical screening uncovered the pain was related to kidney cancer. In this case, the patient was treated over an extended period of four months with a regimen comprising administering a first time-phase dosage in the morning of 18 ml of *P. Pubscens* Fruit concentrate, followed by a second time-phase midday dosage of 17 mls of *H. Diffusa* Willd concentrate, and a third time-phase evening dosage of 20 mls of *H Diffusa* Willd concentrate. All dosages was administered one hour before meals in an oral dosage form. Patient pain observed to decrease over the treatment period.

Case 10—Ovarian Cancer

A 30-year old woman (the patient) presented to a gynecologist with urinary frequency and persistent abdominal bloating. The patient reported maintaining normal activities and a moderate exercise. Abdominal ultrasound showed a complex mass in the right pelvis measuring 4.5×5.0×7.5 cm. Further evaluation scheduled the patient for surgery which the patient underwent having complete resection with no residual disease remaining.

About two-years later, the patient reported having symptoms of persistent abdominal distention and weight loss. The patient described feeling tired and napping during the day. A Computed Tomography (CT) scan showed peritoneal seeding consistent with carcinomatosis.

The patient subsequently approached the applicant for multi-phase combined treatment according to the invention.

The patient was administered a first time-phase morning dosage of 18 mls *P. Pubscens* Fruit concentrate, followed by a second time-phase midday dosage of 16 mls of *H. Diffusa* Willd concentrate, followed by a third time-phase evening dosage of 20 mls of *H. Diffusa* Willd concentrate. All dosages were administered in an oral form to the patient one hour prior to meals.

Within one-month the patient showed signs of maintaining weight, and energy level increased. Further CT scans were performed on the patient and the patient determined as all clear of the carcinomatosis onset. Applicant believes this finding suggest there is a synergistic activity produced by the coordination of these two specific extracts in a multi-phase treatment regimen.

Case 11—Diabetes

In this case, a 76-year old man (the patient) presented with a three-year history of type 2 diabetes. The patient had symptoms indicating hyperglycemia for two-years before diagnosis. The patient had fasting glucose records reading values of 118 127 mg/dl, which described him as indicative of "borderline diabetes". The patient was advised to reduce weight at the time of diagnosis, but no further action was taken.

The patient elected to try the applicant's medication hoping this would assist the patient's weight related issue. The patient commenced treatment on a daily regimen of administration of a first time-phase morning dosage of 20 mls of *P. Pubscens* Fruit concentrate, followed by a second time-phase midday dosage of 16 mls of *H. diffusa* Willd concentrate and a third time-phase evening dosage of 18 mls of *H. Diffusa* Willd concentrate.

The patient conducted regular blood sugar monitoring at home and found sugar levels had stabilized. Further clinical evaluation indicates that extract elicited significant reductions of blood glucose and caused a significant increase in serum insulin in diabetic cases. This suggests there is a promising antidiabetic effectiveness of the extract.

Case 12—Colon Cancer

A man (the patient) diagnosed with colon cancer was treated with the applicant's treatment regimen by administering a first time-phase morning dosage of 18 mls of *P. Pubscens* Fruit concentrate, followed by a second time-phase midday dosage of 18 mls of native *H. Diffusa* Willd concentrate and a third time-phase evening dosage of 18 mls of *H. Diffusa* Willd concentrate. Each of the multi-phase dosages was administered in an oral form one hour prior to each meal time.

At three-months and six-months into the treatment of the invention, a CT scan was performed on the patient. The CT scans, which initially (pre-treatment) had showed a non-obstructive mass in the sigmoid colon that infiltrated the full thickness of the bowel wall and involved adipose tissue, to have decreased in size. At six-months months CT scan, they were no longer detected. The nodules appear to have gone. Concomitantly, the patient reported less fatigue and some improvement in performing daily tasks. This observation suggests the extract is a promising treatment alternative.

Case 13—Herpes Zoster (Shingles)

A male patient presented with flu like symptoms, fatigue, fever chills and headaches. The patient also had a burning pain on the calf of his leg. Upon examination there were rash with blisters, painful to touch. The patient was diagnosed with Herpes Zoster (Shingles).

The patient was treated with the applicant's combined multi-phase treatment regimen by administering a first time-phase morning dosage of 16 mls of *P. Pubscens* Fruit concentrate, followed with a second time-phase midday dosage of 18 mls of *H. Diffusa* Willd concentrate and a third time-phase evening dosage of 18 mls of *H. Diffusa* Willd concentrate. Each dosage was administered in an oral form one hour before meals.

Observations of the patient's progress show that the patient has managed to maintain further onset of the disease with visible signs of the rash gradually fading. Applicant believes this finding is indicative of the extract as a promising treatment for shingles.

Case 14—Liver Cancer

A 39-year old man (the patient) presented with a history of cirrhosis due to long term alcohol abuse. The patient was found to have a solitary lesion in the dome of his liver consistent with hepatocellular carcinoma (HCC). A PET-CT scan suggested hepatic dome carcinoma without evidence of extrahepatic disease Biopsy by ultrasound guided percutaneous needle puncture confirmed the diagnosis of HCC.

The patient was treated with the applicant's invention by administration of a first time-phase morning dosage of 16 mls of *P Pubscens* Fruit concentrate, followed with a second time-phase midday dosage of 18 mls of *H Diffusa* Willd concentrate and a third time-phase evening dosage of 18 mls of *H. Diffusa* Willd concentrate.

Two months after treatment, there was no visual evidence of the acute liver toxicity on CT scans nor was there any residual abnormal activity noted in the previous tumor location. Further scanning at nine months, the tumor continued to be CT negative and no noted side effects exists from the treatment.

Interpretation

EMBODIMENTS

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the coordinated botanical medicament industries.

The invention claimed is:

1. A method of treating liver cancer, ovarian cancer, colon cancer, kidney cancer, lymph cancer, nasal cavity cancer, throat cancer, skin cancer, stomach cancer, prostate cancer, breast cancer, cervical cancer HIV/AIDS, and diabetes comprising:
administering to a subject in need thereof at differential times comprising at least two time-phases, a dosage form in a first dosage of a first therapeutically effective amount of a first plant extract or one of its physiological acceptable forms obtained from *Physalis pubescens* fruit in a pharmaceutically acceptable carrier during a first time-phase;
administering to said subject a dosage form in a second dosage of a therapeutically effective amount of a second plant extract or one of its physiological acceptable forms obtained from *Hedyotis Diffusa* Willd in a pharmaceutically acceptable carrier during a second time-phase; and
administering to said subject a supplementary dosage comprising an effective amount of a plant extract or one of its physiologically acceptable forms obtained from *Hedyotis Diffusa* Willd in a pharmaceutically acceptable carrier in a third time-phase, wherein the supplementary dosage of *Hedyotis Diffusa* Willd or one of its physiologically acceptable forms is administered in a predetermined time-phase cycle after administration of the second plant extract or one of its physiologically acceptable forms;
wherein the first dosage is applied at a first time-phase and the second dosage is applied at a second time-phase spaced from the first time-phase by at least two hours;
wherein *Physalis pubescens* fruit and *Hedyotis Diffusa* Willd of the first dosage and the second dosage are provided in a dosage ratio of between about 1:1 to about 1:5; and
wherein combination of the first and second dosage forms administered in at least the first and second time-phases assist in treatment of abnormal cells for treatment for one or more of the identified cancers.

2. The method according to claim 1, wherein the at least two time-phase treatment of administering a dosage form in a first dosage of a therapeutic effective amount of a first plant extract or one of its physiological acceptable forms at a first time-phase in a day and administering a dosage form in a second dosage of a therapeutic effective amount of a second plant extract or one of its physiological acceptable forms at a second time-phase later in the day is repeated daily for weeks to months to reduce, remove or stabilize the cancer.

3. The method according to claim 1, wherein *Physalis pubescens* fruit of the first dosage of the first time-phase is provided in a dosage of between about 15 to 25 grams.

4. The method according to claim 1, wherein *Hedyotis Diffusa* Willd of the second dosage of the second time-phase is provided in a dosage of between about 15 to 25 grams.

5. The method according to claim 1, wherein the treatment is for one of:
HIV/AIDS, and
diabetes.

6. The method according to claim 1 wherein an effective amount of the plant extract or one of its physiologically acceptable forms obtained from *Physalis pubescens* fruit is administered at a first time-phase, repeated cyclically to maintain an effective amount or concentration systemically.

7. The method according to claim 1 wherein in use an effective amount of the second plant extract or one of its physiologically acceptable forms obtained from *Hedyotis*

*Diffusa* Willd is administered at a second time-phase, repeated cyclically to maintain an effective amount or concentration systemically.

8. The method according to claim 1 wherein an effective amount of the plant extract or one of its physiologically acceptable forms obtained from *Hedyotis Diffusa* Willd is administered at a third time-phase, repeated cyclically to maintain an effective amount or concentration systemically.

* * * * *